United States Patent
Larson et al.

(10) Patent No.: US 7,092,757 B2
(45) Date of Patent: Aug. 15, 2006

(54) MINUTE VENTILATION SENSOR WITH DYNAMICALLY ADJUSTED EXCITATION CURRENT

(75) Inventors: Dennis E. Larson, White Bear Township, MN (US); Douglas R. Daum, Oakdale, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 473 days.

(21) Appl. No.: 10/195,135

(22) Filed: Jul. 12, 2002

(65) Prior Publication Data

US 2004/0049237 A1 Mar. 11, 2004

(51) Int. Cl.
*A61N 1/365* (2006.01)

(52) U.S. Cl. .............................. 607/17; 607/18; 607/24

(58) Field of Classification Search .................. 607/9, 607/17, 24, 28; 600/508–509, 513, 547, 600/554; 128/901
See application file for complete search history.

(56) References Cited

U.S. PATENT DOCUMENTS

| | | |
|---|---|---|
| 3,593,718 A | 7/1971 | Krasner |
| 4,009,721 A | 3/1977 | Alcidi |
| 4,140,132 A | 2/1979 | Dahl |
| 4,228,803 A | 10/1980 | Rickards |
| 4,291,699 A | 9/1981 | Geddes et al. |
| 4,399,820 A | 8/1983 | Wirtzfeld et al. |
| 4,428,378 A | 1/1984 | Anderson et al. |
| 4,510,944 A | 4/1985 | Porges |
| 4,519,395 A | 5/1985 | Hrushesky |
| 4,543,954 A | 10/1985 | Cook et al. |
| 4,562,843 A | 1/1986 | Djordjevich et al. |
| 4,596,251 A | 6/1986 | Plicchi et al. |
| 4,686,987 A | 8/1987 | Salo et al. |
| 4,702,253 A | 10/1987 | Nappholz et al. |
| 4,722,351 A | 2/1988 | Phillipps et al. |
| 4,773,401 A | 9/1988 | Citak et al. |
| 4,781,201 A | 11/1988 | Wright et al. |
| 4,858,611 A | 8/1989 | Elliott |
| 4,899,752 A | 2/1990 | Cohen |
| 4,901,725 A | 2/1990 | Nappholz et al. ........... 128/419 |
| 4,930,518 A | 6/1990 | Hrushesky |
| 4,960,129 A | 10/1990 | dePaola et al. |
| 4,966,146 A | 10/1990 | Webb et al. |
| 5,027,813 A | 7/1991 | Pederson et al. |
| 5,063,927 A | 11/1991 | Webb et al. |
| 5,074,303 A | 12/1991 | Hauck |
| 5,085,215 A | 2/1992 | Nappholz et al. |

(Continued)

FOREIGN PATENT DOCUMENTS

DE 2805482 3/1987

(Continued)

OTHER PUBLICATIONS

Larson, Dennis E., et al., "Minute Ventilation Sensor With Automatic High Pass Filter Adjustment", U.S. Appl. No. 10/306,889, Filed Nov. 27, 2002, 33 pages.

*Primary Examiner*—Carl Layno
(74) *Attorney, Agent, or Firm*—Schwegman, Lundberg, Woessner & Kluth, P.A.

(57) ABSTRACT

A minute ventilation sensing device in which transthoracic impedance is measured with a excitation current waveform at a specified amplitude and frequency. In order reduce interference with the impedance measurement from external noise sources, a noise detection operation may be performed with the amplitude and/or frequency of the excitation current waveform adjusted accordingly.

22 Claims, 8 Drawing Sheets

U.S. PATENT DOCUMENTS

| | | | |
|---|---|---|---|
| 5,105,819 A | 4/1992 | Wollschlager et al. | |
| 5,107,850 A | 4/1992 | Olive | |
| 5,137,019 A | 8/1992 | Pederson et al. | |
| 5,156,147 A | 10/1992 | Warren et al. | |
| 5,174,286 A | 12/1992 | Chirife | 128/419 PG |
| 5,179,946 A | 1/1993 | Weiss | 128/419 D |
| 5,190,035 A | 3/1993 | Salo et al. | |
| 5,197,467 A | 3/1993 | Steinhaus et al. | |
| 5,201,808 A | 4/1993 | Steinhaus et al. | |
| 5,235,237 A | 8/1993 | Leonhardt | |
| 5,235,976 A | 8/1993 | Spinelli | |
| 5,249,572 A | 10/1993 | Bonnet | |
| 5,271,395 A | 12/1993 | Wahlstrand et al. | |
| 5,273,034 A | 12/1993 | Nilsson | |
| 5,284,136 A | 2/1994 | Hauck et al. | |
| 5,300,093 A | 4/1994 | Koestner et al. | |
| 5,303,702 A | 4/1994 | Bonnet et al. | |
| 5,314,449 A | 5/1994 | Lindgren | |
| 5,318,597 A | 6/1994 | Hauck et al. | 607/20 |
| 5,379,776 A | 1/1995 | Murphy et al. | |
| 5,383,473 A | 1/1995 | Moberg | |
| 5,391,190 A | 2/1995 | Pederson et al. | |
| 5,423,870 A | 6/1995 | Olive et al. | |
| 5,423,883 A | 6/1995 | Helland | |
| 5,431,687 A | 7/1995 | Kroll | |
| 5,441,524 A | 8/1995 | Rueter et al. | |
| 5,466,245 A | 11/1995 | Spinelli et al. | |
| 5,469,859 A | 11/1995 | Tsoglin et al. | |
| 5,480,412 A | 1/1996 | Mouchawar et al. | |
| 5,490,323 A | 2/1996 | Thacker et al. | 29/625 |
| 5,501,702 A | 3/1996 | Plicchi et al. | |
| 5,507,785 A | 4/1996 | Deno | |
| 5,522,860 A * | 6/1996 | Molin et al. | 607/20 |
| 5,524,632 A | 6/1996 | Stein et al. | |
| 5,531,772 A | 7/1996 | Prutchi | |
| 5,562,711 A | 10/1996 | Yerich et al. | |
| 5,562,712 A | 10/1996 | Steinhaus et al. | |
| 5,626,622 A | 5/1997 | Cooper | |
| 5,626,624 A | 5/1997 | Schaldach et al. | |
| 5,685,316 A | 11/1997 | Schookin et al. | |
| 5,713,933 A | 2/1998 | Condie et al. | |
| 5,718,235 A | 2/1998 | Golosarsky et al. | |
| 5,722,997 A | 3/1998 | Nedungadi et al. | 607/28 |
| 5,749,900 A | 5/1998 | Schroeppel et al. | |
| 5,782,884 A | 7/1998 | Stotts et al. | |
| 5,792,194 A | 8/1998 | Morra | |
| 5,800,470 A | 9/1998 | Stein et al. | |
| 5,817,135 A | 10/1998 | Cooper et al. | 607/17 |
| 5,817,136 A | 10/1998 | Nappholz et al. | |
| 5,824,020 A | 10/1998 | Cooper | |
| 5,824,029 A | 10/1998 | Weijand et al. | 607/122 |
| 5,836,975 A | 11/1998 | DeGroot | |
| 5,836,976 A | 11/1998 | Min et al. | |
| 5,891,044 A | 4/1999 | Golosarsky et al. | |
| 5,978,707 A | 11/1999 | Krig et al. | |
| 6,044,294 A | 3/2000 | Mortazavi et al. | 600/547 |
| 6,049,735 A | 4/2000 | Hartley et al. | |
| 6,076,015 A | 6/2000 | Hartley et al. | 607/20 |
| 6,151,524 A | 11/2000 | Krig et al. | |
| 6,161,042 A | 12/2000 | Hartley et al. | 607/20 |
| 6,317,632 B1 | 11/2001 | Krig et al. | |
| 6,463,326 B1 | 10/2002 | Hartley et al. | 607/20 |
| 6,522,914 B1 | 2/2003 | Huvelle | |
| 6,574,506 B1 | 6/2003 | Kramer et al. | |
| 2002/0107552 A1 | 8/2002 | Krig et al. | |
| 2002/0123768 A1 | 9/2002 | Gilkerson | |
| 2002/0123769 A1 | 9/2002 | Panken et al. | |
| 2003/0069609 A1 | 4/2003 | Thompson | |
| 2003/0105499 A1 | 6/2003 | Hartley et al. | 607/17 |
| 2004/0102908 A1 | 5/2004 | Larson et al. | |
| 2004/0116820 A1 | 6/2004 | Daum et al. | |

FOREIGN PATENT DOCUMENTS

| | | |
|---|---|---|
| EP | 0003567 | 8/1979 |
| EP | 0360412 | 3/1990 |
| EP | 0401962 | 12/1990 |
| EP | 447024 | 9/1991 |
| EP | 0555988 | 8/1993 |
| EP | 0597459 | 5/1994 |
| EP | 0617980 | 10/1994 |
| EP | 702977 A | 3/1996 |
| EP | 0748638 | 12/1996 |
| EP | 765632 | 4/1997 |
| WO | WO-93/02746 | 2/1993 |
| WO | WO-94/06512 | 3/1994 |
| WO | WO-98/14240 | 4/1998 |
| WO | WO 99/43385 * | 9/1999 |

* cited by examiner

MINUTE VENTILATION SENSOR WITH DYNAMICALLY ADJUSTED EXCITATION CURRENT

FIELD OF THE INVENTION

This invention pertains to implantable medical devices such as cardiac pacemakers. In particular, the invention relates to a device and method for improved sensing of physiological variables by impedance measurements.

BACKGROUND

Implantable medical devices are commonplace today for treating cardiac dysfunction. Cardiac pacemakers, for example, are implantable medical devices that replace or supplement a heart's compromised ability to pace itself (i.e., bradycardia) due to chronotropic incompetence or a conduction system defect by delivering electrical pacing pulses to the heart. Pacemakers can deliver pacing pulses asynchronously at a fixed rate or synchronously in a manner that depends upon sensed intrinsic beats. Most pacemakers today are operated in some sort of synchronous mode where the pacing pulses are delivered upon the expiration of escape intervals that are reset by sensed intrinsic depolarizations of the heart. The pacing rate is then determined by the programmed escape intervals of the pacemaker and is referred to as the lower rate limit or LRL in the case of ventricular pacing.

In chronotropically competent patients in need of ventricular pacing, atrial triggered modes where ventricular pacing is controlled by sensed atrial beats are desirable because they allow the pacing to track the physiologically normal atrial rhythm, which then causes cardiac output to be responsive to the metabolic needs of the body. Atrial triggered modes are contraindicated, however, in patients prone to atrial fibrillation or flutter or in whom a reliable atrial sense cannot be obtained. In pacemaker patients who are chronotropically incompetent (e.g., sinus node dysfunction) or in whom atrial triggered modes are contraindicated, the heart rate is dictated solely by the pacing rate of the pacemaker in the absence of faster intrinsic cardiac activity.

Pacing the heart either asynchronously at a fixed rate or synchronously at a rate determined by the LRL setting of the pacemaker, however, does not allow the heart rate to increase with increased metabolic demand. If the heart is paced at a constant rate, severe limitations are imposed upon the patient with respect to lifestyle and activities. It is to overcome these limitations and improve the quality of life of such patients that rate-adaptive pacemakers have been developed. Such pacemakers are rate-controlled in accordance with a measured physiological variable that corresponds to exertion level and is indirectly reflective of the body's metabolic rate. The measured exertion level is mapped to a particular target heart rate by a specified rate-response factor, the inverse of the target rate then being used as the escape interval for atrial or ventricular pacing. Minute ventilation is the amount of air breathed by a subject over a minute or other specified period of time and can be computed as the product of respiratory rate and tidal volume. Minute ventilation is a good indicator of the rate of oxygen consumption and hence is one of the best measurements of a patient's exertion level.

Rate-adaptive pacemakers may use an impedance technique for measuring minute ventilation. The blood and body fluids within the thoracic cavity constitute a volume conductor, and the electrical impedance between any two points in the thoracic cavity is dependent upon the volume of blood and/or air between the two points. The impedance can be measured by impressing a constant current field within the cavity and then measuring the potential difference between the two points. By appropriate placement of voltage sensing electrodes, an impedance signal can be produced that corresponds to the movement of air into and out of the lungs as a subject breathes. Thus, in order to measure minute ventilation, a constant excitation current may be made to flow between two excitation current electrodes located within the thoracic cavity, and the voltage difference between two appropriately located voltage sense electrodes in the cavity is measured. The resulting impedance signal varies in accordance with the subject's ventilation, and the minute ventilation can be derived therefrom. In order to conserve energy and avoid undesirable cardiac stimulation, the excitation current is injected as short current pulses of limited amplitude so that the impedance signal is a discrete time signal. Interference with this impedance signal by environmental noise, however, can compromise the ability of the impedance measurement to accurately reflect the patient's actual ventilation, especially at low excitation current levels. The present application addresses these and other problems.

SUMMARY

The present invention relates to an apparatus and method for minute ventilation sensing in which the excitation current is adjusted in accordance with a detected noise level. A minute ventilation sensing device incorporating the invention may include an exciter for supplying excitation current between excitation current electrodes as a bipolar excitation current waveform at a specified excitation frequency and amplitude, wherein the excitation current waveform is output as a strobe made up of a specified number of excitation current waveform cycles with each strobe repeated at a specified strobing frequency. Voltage sense electrodes generate a voltage sense signal corresponding to a potential difference between two points in the thoracic cavity which is sampled during the excitation waveform strobe at a specified sampling rate that corresponds to the excitation frequency. A weighted average of the voltage sense signal samples of each strobe is then generated with a filter coefficient for each sample that is positive or negative in accordance with the polarity of the excitation current waveform. The result is that an impedance portion of the voltage sense signal is low-pass filtered while an external field portion of the voltage sense signal is high-pass filtered. The demodulated voltage sense signal sample is filtered into a ventilation band to thereby generate a ventilation signal, and a signal proportional to minute ventilation is then derived from the ventilation signal. In accordance with the invention, a noise detection operation may be performed by the device such that the voltage sense signal is sampled when no excitation current is supplied. The samples are then processed to detect a noise level, and the excitation current is adjusted in accordance with the detected noise level.

DETAILED DESCRIPTION

The present invention is a device and method for reducing the effects of external noise upon minute ventilation sensing. It may be applied in any type of apparatus utilizing impedance measurement as a technique for sensing minute ventilation, including cardiac rhythm management devices for delivering therapy to the heart as well as monitoring devices. The invention may be incorporated into a number of minute ventilation sensing systems, a particular one of which is described in U.S. Pat. No. 6,161,042 (referred to herein as the '042 patent), assigned to the assignee of the present application and hereby incorporated by reference in its entirety.

1. Minute Ventilation Sensing by Impedance Measurement

Figure 1:
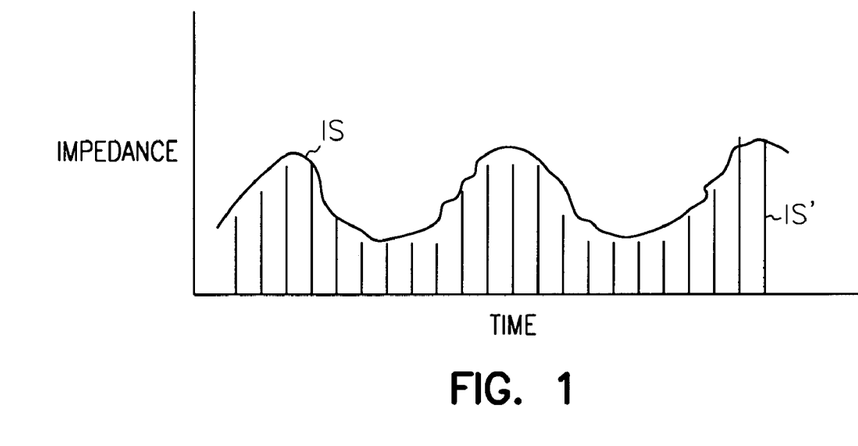
FIG. 1 shows an example of an impedance signal.

As noted above, the electrical impedance of a conductive path between two points that includes part of the thoracic cavity varies in accordance with a subject's respiration. If the voltage between two voltage sense electrodes in the thoracic cavity were measured while a constant excitation current flows between two current source electrodes, a voltage signal corresponding to the impedance between the sense electrodes would be produced. FIG. 1 shows such a transthoracic impedance signal IS that represents the time-varying impedance between the two sense electrodes while the subject breathes as would be generated by a continuous (i.e., DC) constant excitation current. However, it is preferable to inject the excitation current in the form of a pulse train with narrow pulse-widths in order to conserve battery energy. The impedance signal produced at the voltage sense electrodes is then a pulse train at the excitation frequency that is amplitude-modulated by the impedance signal IS. The resulting signal can also be regarded as a discrete-time impedance signal IS' with each signal value representing samples of the continuous impedance signal IS taken at a sampling rate equal to the excitation frequency.

Before deriving the minute ventilation, the impedance signal is filtered to remove both low and high frequency components. The impedance signal thus filtered will be referred to as the ventilation signal. The low frequency components of the impedance signal include both a zero frequency or DC voltage that represents the impedance at full expiration and lower frequency voltages that represent impedance changes due to the slow changes in residual volume of the lungs that occur as the subject alternates between deep and shallow breathing. The high frequency components of the impedance signal include both voltages representing impedance changes resulting from the changes in ventricular blood volume as the heart beats and voltages caused by additional current fields produced from external noise sources. These components can be removed with a bandpass filter or a combination of low-pass and high-pass filtering. Exemplary lower and upper cutoff frequencies for such filtering could be on the order of 0.05 and 1 Hz, respectively, which thus define a ventilation band in which the ventilation signal is found. After filtering the impedance signal to remove the unwanted frequency components, the resulting ventilation signal is directly reflective of the movement of air into and out of the lungs. The minute ventilation can then be derived from the ventilation signal by a number of different methods. For example, the signal can be filtered to derive both a respiratory rate and an average tidal volume, the product of which is the minute ventilation. Alternatively, successive peak-to-peak transitions of the signal, each of which represents the quantity of air inspired during a breath, can be summed over a specified period of time to result in a minute ventilation value.

Figure 2:
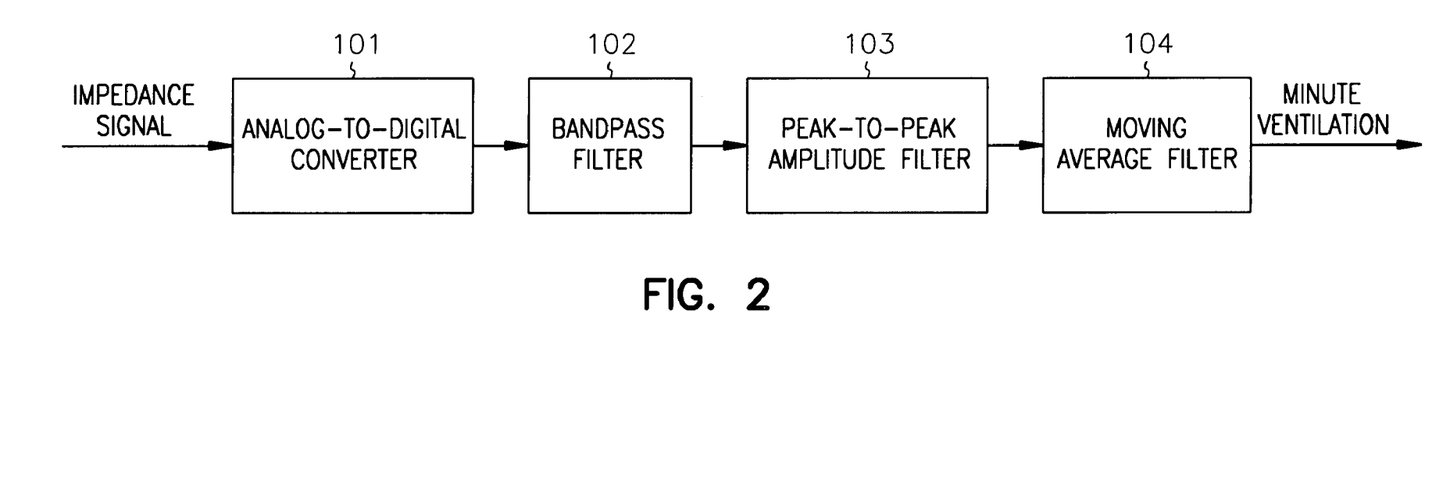
FIG. 2 is a diagram of exemplary functional circuitry for deriving minute ventilation from an impedance signal.

The impedance signal can be processed in either the analog or digital domain or with a combination of digital and analog processing in order to compute the minute ventilation. For example, the discrete time signal IS' generated by the voltage sense electrodes when excitatory current pulses are output can be low-pass filtered to remove the pulse train carrier waveform. The resulting analog waveform can then be further filtered to derive the ventilation signal as described above. The additional filtering can be performed in the analog domain, or the analog signal can be sampled and converted into a digital signal that can be processed in the digital domain. Alternatively, the values of the discrete time signal IS', which correspond to measurements of the voltage between the voltage sense electrodes during an excitation current pulse, can be digitized and processed entirely in the digital domain. FIG. 2 is a block diagram showing one example of how the impedance signal IS' may be further processed either in the analog or digital domain to derive the minute ventilation. A digital bandpass filter 102 (or, equivalently, a combination of low and high pass filters) filters the impedance signal IS' to generate the ventilation signal VS. A peak-to-peak transition filter 103 then derives successive amplitudes of peak-to-peak transitions of the VS waveform that represent inspirations. Each such peak-to-peak transition amplitude is proportional to the tidal volume during a single breath. The successive peak-to-peak transition amplitudes are then filtered by a moving average filter 104 with a specified averaging period to derive a signal proportional to the minute ventilation.

2. Exemplary System Description

Figure 3:
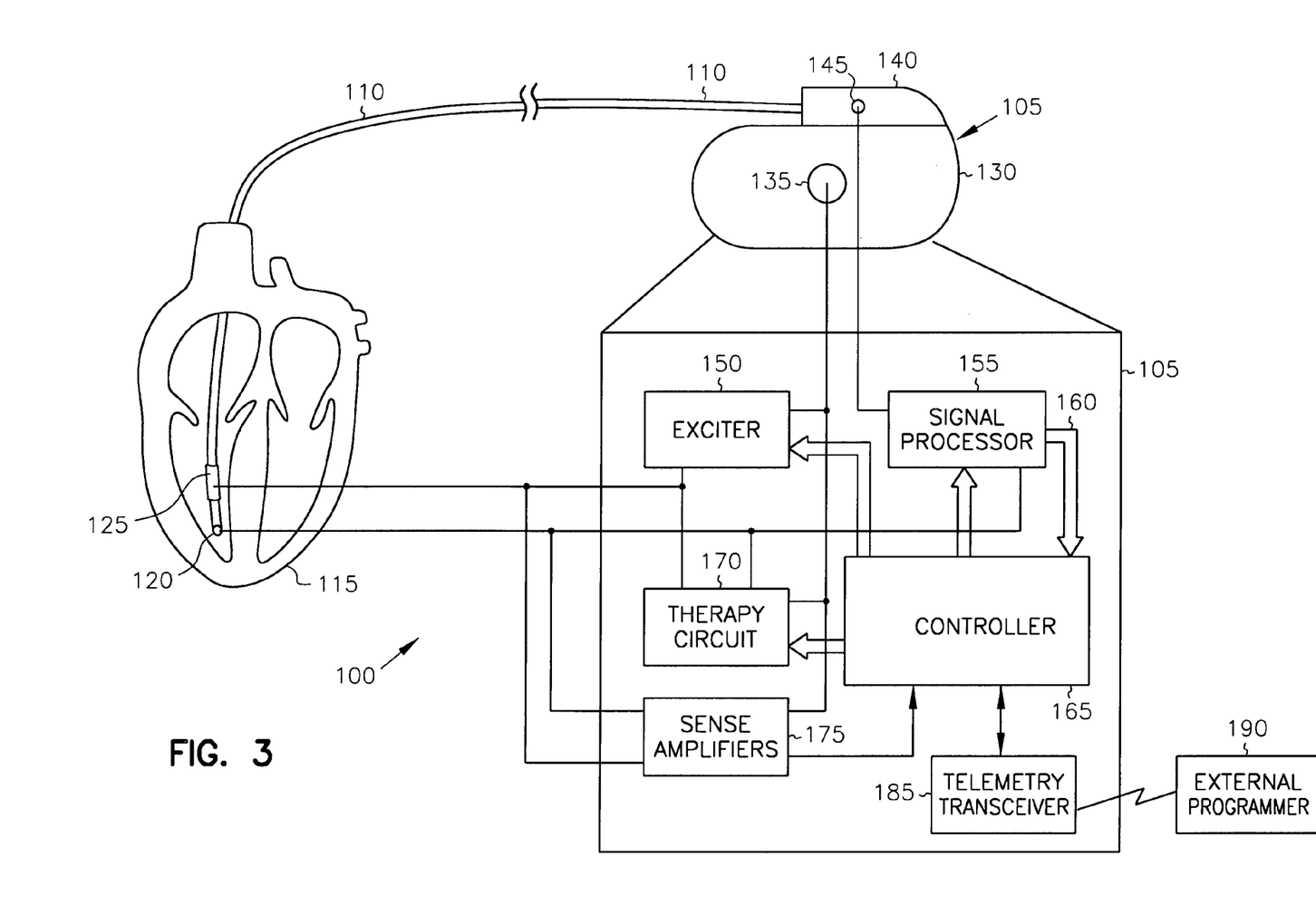
FIG. 3 illustrates an exemplary cardiac rhythm management device according to the present invention.

FIG. 3 is a schematic/block diagram illustrating one embodiment of a cardiac rhythm management system 100 according to the present invention. The illustrated system includes a cardiac rhythm management device 105 and a lead 110 for communicating voltage signals between device 105 and electrodes disposed near or in the heart 115. Device 105 may be, for example, a pacemaker capable of delivering bradycardia and/or antitachycardia pacing, cardioverters, an implantable cardioverter/defibrillator, a combination pacemaker/defibrillator, a drug delivery device, and any other cardiac rhythm management device capable of providing therapy to heart 115. The device 105 includes a controller 165 which may be made up of discrete circuit elements but is preferably a processing element such as a microprocessor. The controller controls the delivery of stimulation to the heart via therapy circuit 170, processes signals reflecting cardiac activity from sense amplifiers 175, and processes impedance measurement signals from signal processor 155. As described above, the impedance measurement signals are used to derive a minute ventilation signal that is used to modulate the pacing rate during bradycardia pacing. Also interfaced to the controller 165 is a telemetry transceiver 185 capable of communicating with an external programmer 190.

Cardiac rhythm management devices may be external to the patient but are usually implanted in a pectoral or abdominal region with one or more leads threaded through the upper venous system to reach the heart. FIG. 3 shows tip electrode 120 and ring electrode 125 separately coupled to device 105 via conductors within multiconductor lead 110. The device 105 includes a hermetically sealed housing 130, formed from a conductive metal, such as titanium. Housing 130 (also referred to as a "case" or "can") may be substantially covered over its entire surface by a suitable insulator, such as silicone rubber, except for at a window that forms a third electrode, referred to as a "case" or "can" electrode 135. A header 140 is mounted on housing 130 for receiving lead 110. The header may be formed of an insulative material, such as molded plastic and also includes a fourth electrode, referred to as indifferent electrode 145. A device may have one or multiple leads with electrodes disposed in the right atrium or ventricle or in a cardiac vein for sensing cardiac activity and/or delivering electrical stimulation to the heart. For example, the tip and ring electrodes may be used together by the therapy circuit 170 and/or sense amplifiers 175 for bipolar pacing/sensing of the heart or in combination with the case or indifferent electrode for unipolar pacing/sensing. Of primary interest here, however, are electrodes used for delivering excitation current to the thorax and for sensing an impedance signal resulting from the current field. Such electrodes may be the same electrodes used for delivering therapy or may be separate electrodes.

Device 105 includes an exciter 150 for delivering excitation current between a selected pair of excitation current electrodes. A current field is thus imposed in the thoracic cavity so that the potential difference between a selected pair of voltage sense electrodes, also located within the thoracic cavity, will be proportional to the impedance between the electrodes. In the example of FIG. 1, the excitation current electrodes are the ring electrode 125 and case electrode 135, shown as connected to the exciter 150. The voltage sense electrodes are the tip electrode 120 and the indifferent electrode 145, shown as electrically connected to the signal processor 155. Thus, in this embodiment, the excitation current electrodes are different from the voltage sense electrodes which advantageously reduces the magnitude of the baseline component of the transthoracic impedance signal, thereby increasing the relative contribution of the ventilation component of the transthoracic impedance signal, and increasing the signal-to-noise ratio (SNR). Alternatively, the same electrodes could be used for delivering the excitation current and sensing the voltage induced thereby. Other embodiments may use different combinations of these or other electrodes as the excitation current and voltage sensing electrodes.

Exciter and Excitation Current Waveform

Figure 4:
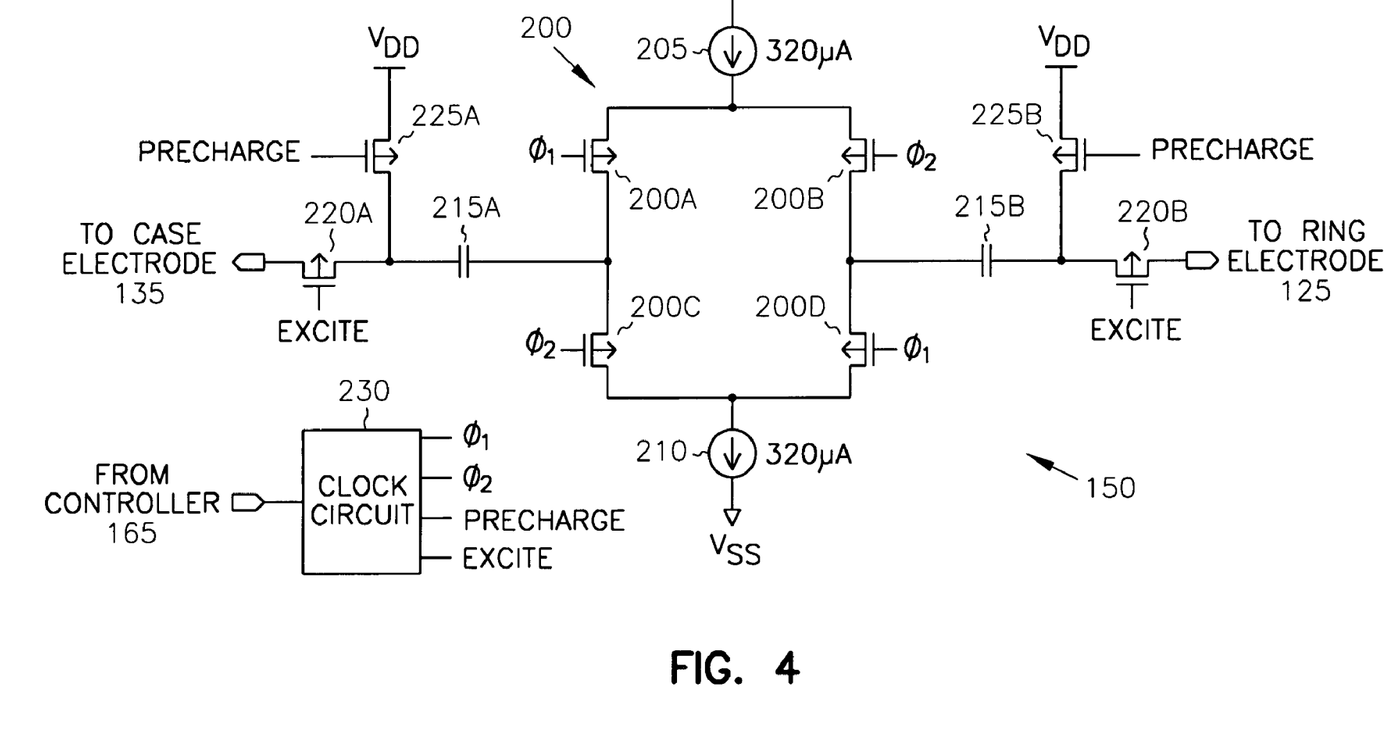
FIG. 4 is illustrates the components of an exemplary exciter for delivering electrical excitation current.

FIG. 4 is a schematic diagram illustrating one embodiment of particular elements included within exciter 150 for delivering excitation current in the form of a carrier waveform that is modulated by transthoracic impedance changes. A bridge switcher 200 includes switches 200A, 200B, 200C, and 200D that may be implemented as transistors, such as p-channel metal-oxide semiconductor (PMOS) field-effect transistors (FETs) or any other suitable switches. The exciter 150 also includes an adjustable current source 205 and current sink 210, each of which may be implemented with transistors in a regulated cascode or other suitable configuration. Switcher 200 is electrically coupled to case electrode 135 and ring electrode 125 through respective dc blocking capacitors 215A and 215B and respective switches 220A and 220B (e.g., PMOS transistors). Switches 225A and 225B (e.g., PMOS transistors) precharge respective capacitors 215A and 215B. Exciter 150 also includes a clock circuit 230 that receives one or more control signals from controller 165 and provides signals to the control terminals of each of switches 200A–D, 220A–B, and 225A–B. The control signals from the controller 165 to the clock circuit cause the exciter to output a bipolar excitation waveform at a specified excitation frequency and for a specified duration. As explained below, in a preferred embodiment, the excitation waveform is output in the form of a strobe made up of a specified number of excitation current waveform cycles with each strobe repeated at a specified strobing frequency.

Figure 5:
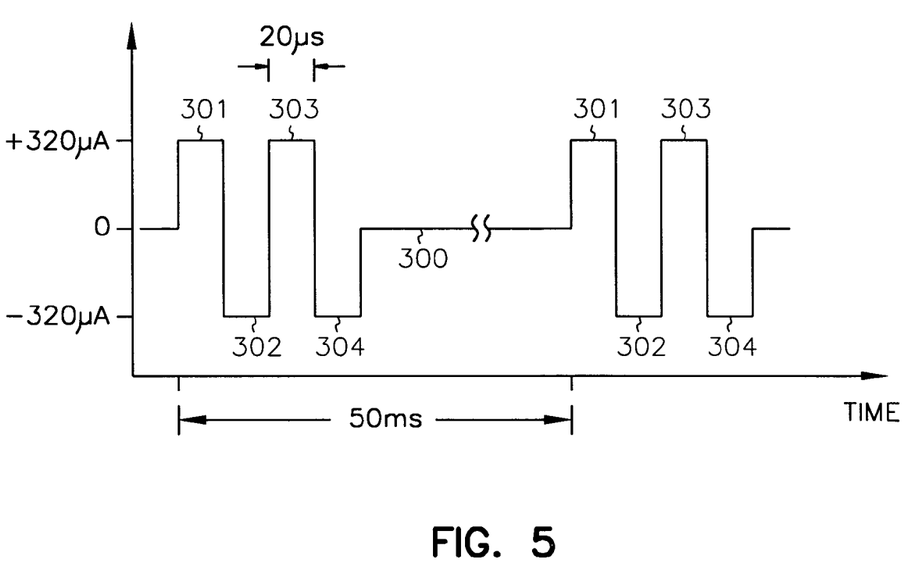
FIG. 5 illustrates a current waveform resulting from operation of an exciter according to one embodiment of the invention.

FIG. 5 illustrates an exemplary excitation current waveform 300 as may be generated by exciter 150 between case electrode 135 and ring electrode 125 in a particular embodiment. Waveform 300 is a multiphase stimulus that is a bipolar square wave strobe made up of four current pulses 301, 302, 303, and 304 in sequentially alternating polarity/direction, each current pulse being a phase of the multiphase stimulus. In the embodiment illustrated in FIG. 5, pulses 301–304 form a square wave having a carrier frequency of approximately 25 kilohertz where each pulse has a duration of 20 microseconds. Also in this embodiment, the four pulse sequence 301–304 is repeated at a strobing frequency of approximately 20 Hertz (i.e., a 50 millisecond time interval). Other suitable durations of current pulses 301–304 could also be used to result in a different carrier frequency, and other suitable strobing frequencies could be used. As explained in more detail below, the voltage sense signal waveform may be sampled during each phase (i.e., during each current pulse 301, 302, 303, and 304) of a strobe so that the sampling rate is twice the excitation frequency. Other embodiments may employ a sampling rate that is differently related to the excitation frequency. The samples of each strobe are then filtered by a demodulator that computes a weighted average of the samples with specified filter coefficients. As explained below, due to the bipolar nature of the excitation current waveform, the demodulator has the effect of filtering out components of the voltage sense signal due to external fields while averaging the impedance signal component of the voltage sense signal. The demodulated voltage sense signal samples thus constitute samples of the impedance signal at a sampling rate equal to the strobing frequency. The strobing frequency should therefore be sufficiently high so as to provide adequate sampling of ventilation or other information carried by the transthoracic impedance signal contained within the voltage sense signal. Such ventilation information can appear at frequencies as high as approximately 1 Hertz, depending on the patient's breathing rate. The strobing frequency should also minimize aliasing of a "stroke volume" component of the impedance signal (i.e., a portion of the transthoracic impedance signal that varies along with the patient's heartbeat instead of the patient's breathing rate) and which can have frequencies as high as approximately 3 Hertz, depending on the patient's heart rate. In order to avoid aliasing the stroke volume component of the impedance signal into the ventilation band, the strobing frequency should be at least twice the highest frequency component expected to be in the impedance signal in accordance with the Nyquist criterion.

The amplitude of current pulses 301–304 is controlled by the controller 165 and is preferably set at some minimum value that provides enough excitation to obtain an adequate voltage response signal while minimizing current drain of the implanted device 105, thereby increasing its implanted longevity. The amplitude of the excitation current pulses should also be minimized in order to prevent unwanted cardiac stimulation and to prevent false sensing of the pulses by the sensing channels of the device where the current pulses are misinterpreted as cardiac activity. For example, in one embodiment, the amplitude of the current pulses 301–304 is selected to be approximately 320 microampere, but other current pulse amplitudes may also be employed. As explained below, the current pulse amplitude may be adjusted by the controller 165 in accordance with a detected noise level so as to maintain an adequate signal-to-noise ratio.

Prior to each sequence of current pulses 301–304, dc blocking capacitors 215A–B are precharged by a bias circuit, such as by turning on switches 200A–D and 225A–B, with switches 220A–B being off. Current source 205 and current sink 210 establish the operating point of a terminal of each of dc blocking capacitors 215A–B that is coupled to switcher 200. After precharging, switches 225A–B are turned off. Next, pulse 301 is produced by turning on switches 200A, 200D, and 220A–B, such that current delivered by current source 205 leaves case electrode 135. The current returns through ring electrode 125, and is sunk by current sink 210. Next, pulse 302 is produced by turning on switches 200B–C and 220A–B, such that current delivered by current source 205 leaves ring electrode 125. The current returns through case electrode 135, and is sunk by current sink 210. Next, pulse 303 is produced by again turning on switches 200A, 200D, and 220A–B, such that current delivered by current source 205 leaves case electrode 135. The current returns through ring electrode 125, and is sunk by current sink 210. Next, pulse 304 is produced by again turning on switches 200B–C and 220A–B, such that current delivered by current source 205 leaves ring electrode 125. The current returns through case electrode 135, and is sunk by current sink 210. Switches 220A–B, 200A–D, and 225A–B are turned off until precharging for another four current pulse sequence 301–304, which is delivered approximately 50 milliseconds later in the embodiment illustrated in FIG. 5. Preferably, clock circuit 230 provides non-overlapping control signals to switches 225A–B and switches 220A–B so that switches 225A–B are not turned on at the same time as switches 220A–B. This avoids any coupling of either of case electrode 135 and ring electrode 125 to the positive power supply voltage $V_{DD}$.

Signal Processor

Figure 6A:
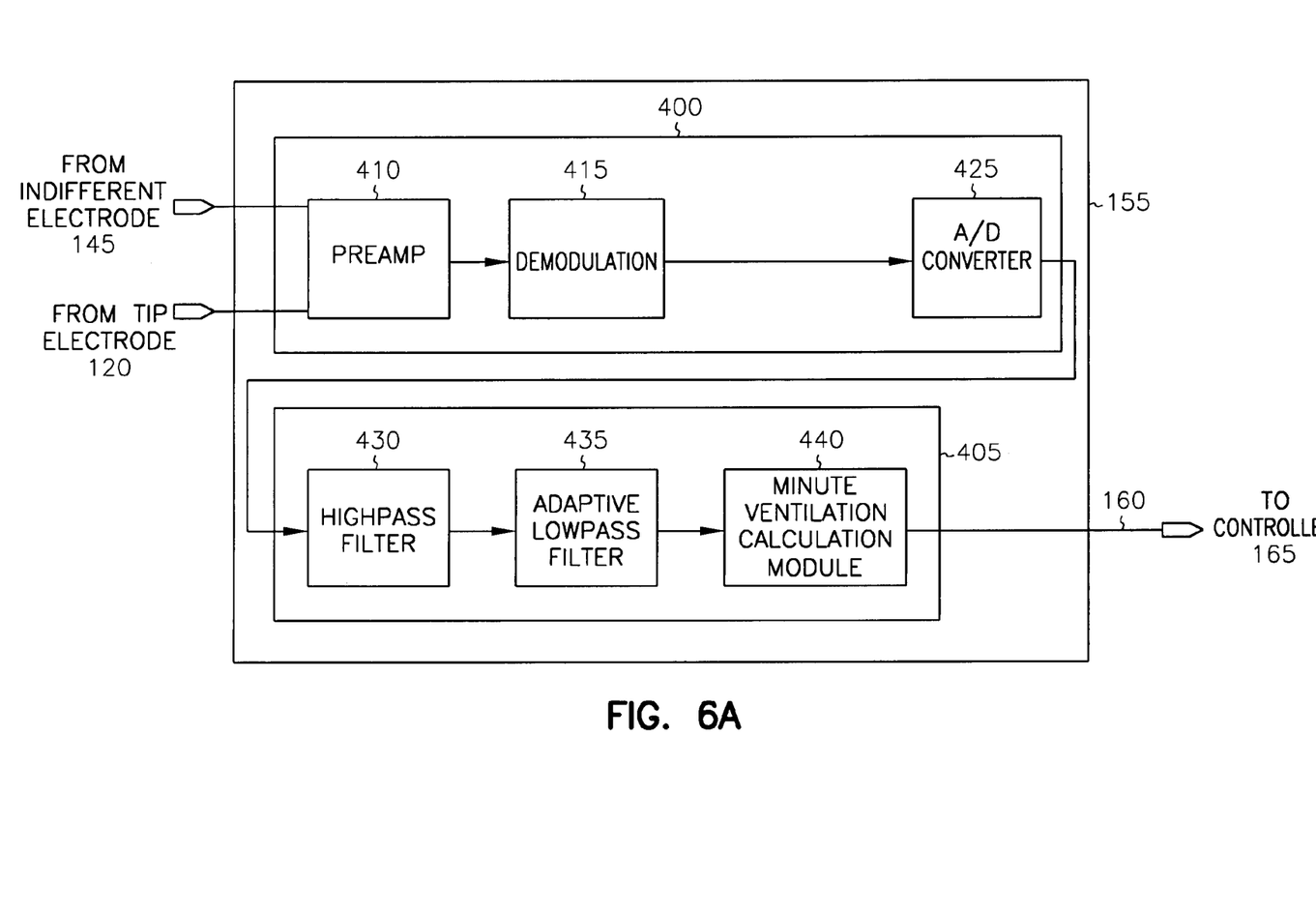
FIG. 6A is a block diagram illustrating one embodiment of a signal processor.

FIG. 6A is a block diagram illustrating one embodiment of portions of signal processor 155. Signal processor 155 includes analog signal processing circuit 400 and digital signal processing circuit 405. Inputs of a preamplifier 410 of analog signal processing circuit 400 are electrically coupled to each of indifferent electrode 145 and tip electrode 120 for receiving a voltage sense signal in response to the above-described stimuli provided by exciter 150. An exemplary preamplifier is described in detail in the '042 patent, particularly with reference to FIG. 5 of that document. Analog signal processing circuit 400 also includes demodulator 415 that samples the analog output of preamplifier 410 and provides an output signal received by analog-to-digital (A/D) converter 425. An output signal from A/D converter 425 is received at highpass filter 430, and an output signal from highpass filter 430 is received by adaptive lowpass filter 435. Minute ventilation calculation module 440 receives an output signal from adaptive lowpass filter 435, and provides a calculated minute ventilation signal at node 160 to controller 165.

Figure 6B:
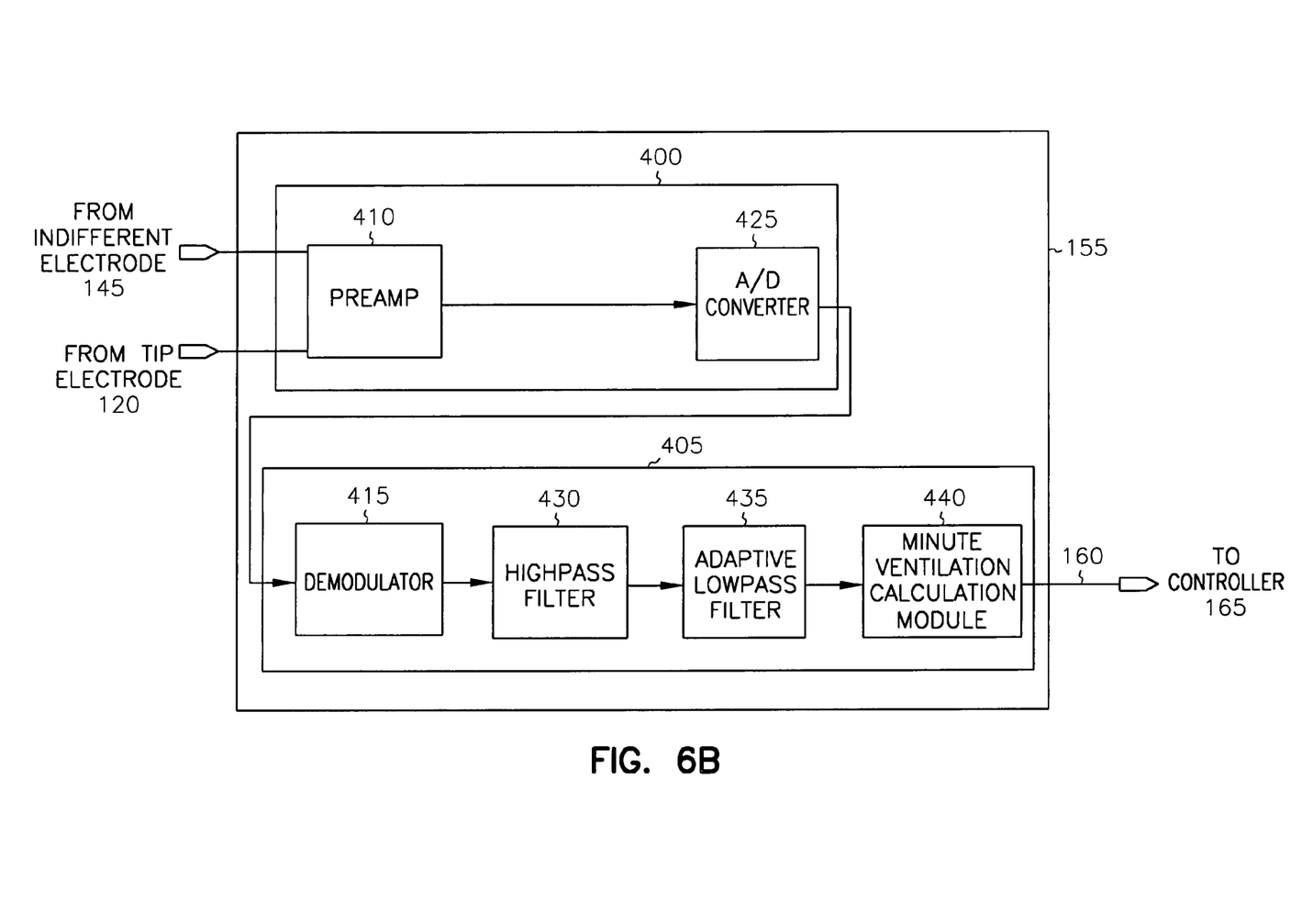
FIG. 6B is a block diagram illustrating an embodiment of a completely digital signal processor.

FIG. 6B shows another embodiment of the signal processor in which the analog processing circuit is made up of preamplifier 410 and A/D converter 425, with the functionality of the demodulator 415 being moved to the digital processing circuit. In this embodiment, the voltage sense signal is digitized immediately after preamplification, and the demodulator 415 is a digital filter. In either of the embodiments shown in FIGS. 6A or 6B, the digital signal processing circuit 405 may be implemented as coded instructions executed by controller 165 or as separately implemented hardware portions dedicated to performing the digital signal processing tasks described below.

Demodulator

The demodulator portion of the signal processor removes the excitation current waveform from the voltage sense signal samples of each strobe by low-pass filtering of the voltage sense signal samples. As explained more fully below, a discrete-time low-pass filter will have the further advantageous effect of high-pass filtering external field noise from the voltage sense signals due to the bipolar nature of the excitation current waveform.

As shown in FIGS. 6A and 6B, the demodulator 415 may be implemented in either the digital or analog domain. In FIG. 6A, the analog demodulator 415 includes sampling circuitry for converting the output of the preamplifier into a discrete-time analog signal. In FIG. 6B, on the other hand, the analog-to-digital converter 425 includes circuitry for both sampling and digitizing the output of the preamplifier, the digitized voltage sense signal then being input to the digital demodulator 415. In either case, the sampling is synchronized to the excitation current waveform. Thus, referring to FIG. 5, the output of preamplifier 410 is sampled some time during each of current pulses 301–304. Demodulator 415 then combines these four samples into a single value using a weighted average to effect both low-pass filtering of the impedance signal and high-pass filtering of external field noise.

In one embodiment, the demodulator filter is a finite impulse responses filter that computes a weighted average of the strobe samples. The weighted average is formed by weighting the second and third samples, obtained from respective current pulses 302 and 303, by a factor of approximately 3.0 relative to the first and fourth samples, obtained from respective current pulses 301 and 304. A transfer function representing this embodiment of demodulator 415 is described in the z-domain as:

$$H(z)=K(z^{-3}-3z^{-2}+3z^{-1}-1)$$

where K is a gain associated with the filtering. In a digital demodulator 415, the transfer function can be implemented directly as code. The transfer function can be implemented in one embodiment of an analog demodulator as a switched capacitor circuit that also performs a sampling function.

Figure 7:
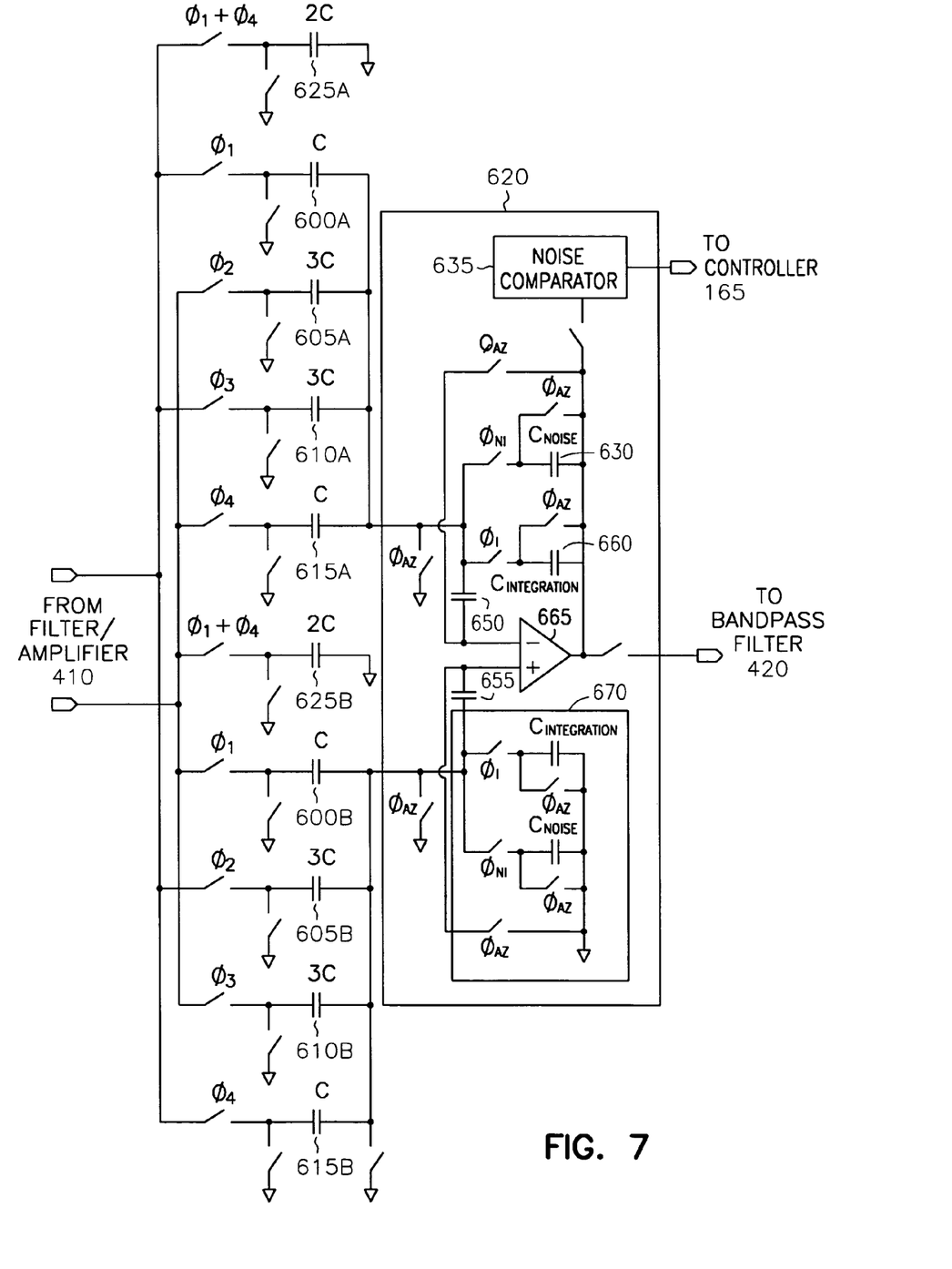
FIG. 7 is a schematic diagram illustrating one embodiment of a demodulator.

FIG. 7 is a schematic diagram illustrating one embodiment of a switched-capacitor analog demodulator 415. The output signal from preamplifier 410 is sampled onto capacitors 600A–B in response to current pulse 301, onto capacitors 605A–B in response to current pulse 302, onto capacitors 610A–B in response to current pulse 303, and onto capacitors 615A–B in response to current pulse 304. Sampling onto the capacitors is effected by closure of solid-state sampling switches in response to switch-closure inputs $\varnothing_1$ through $\varnothing_4$ that correspond to the phase of the excitation current waveform during which the switch is closed, 301 through 304, respectively. The switch-closure inputs are generated, for example, by a clock circuit synchronized with the exciter 150. Capacitors 605A–B and 610A–B provide 3 times the capacitance value of capacitors 600A–B and 615A–B, in order to provide the above-described weighting of the samples. After the weighted sampling of the output of preamplifier 410 in response to the four current pulses 301–304, these weighted samples are summed by switched-capacitor integrator 620 (also referred to as a summer).

Also shown in FIG. 7 are dummy capacitors 625A–B. Each of dummy capacitors 625A–B has a capacitance value that is twice that of one of capacitors 600A–B, and twice that of one of capacitors 615A–B. Dummy capacitors 625A–B are switched in during sample of current pulses 301 and 304. As a result, demodulator 415 presents the same load capacitance to preamplifier 410 during sampling of each of the four current pulses 301–304. As seen in FIG. 7, however, the charge that is sampled onto dummy capacitors 625A–B is not included in the weighted sample (i.e., the resulting charge is not included in the integration provided by integrator 620). Furthermore, it is understood that, in one embodiment, the capacitors shown in FIG. 7 are initialized (e.g., discharged) prior to sampling any particular sequence of current pulses 301–304.

Integrator 620 also includes input capacitors 650 and 655, which are autozeroed by switches, as illustrated, during the clock phase $\phi_{AZ}$. An integration capacitor 660, which is in the feedback path around operational amplifier 665, sums the weighted samples obtained in response to the four current pulses 301–304 during an integration clock phase $\phi_I$. A noise sampling/integration capacitor 630, which is also in the feedback path around operational amplifier 665, may be used instead to sum the weighted samples obtained in the absence of delivered current pulses during a noise integration clock phase $\phi_{NI}$, as described below. Integrator 620 also provides a matching network 670 on the other input of operational amplifier 665 for matching the above-described switched capacitor operation.

Analog-to-Digital (A/D) Converter

A/D converter 425 receives the output signal of demodulator 415 and provides a resulting digitized output signal to highpass filter 430 of digital signal processing circuit 405. In one embodiment, A/D converter 425 is implemented as an 8-bit, successive approximation type switched-capacitor A/D converter having an input range of approximately 1 Volt. According to one aspect of the invention, A/D converter 425 provides one 8-bit digital word corresponding to each sequence of four current pulses 301–304 delivered by exciter 150. Many different implementations of A/D converter 425 will be suitable for use in the present invention, including different A/D converter resolutions.

Digital Signal Processing Circuit

The digital processing circuit filters the highpass-filtered and demodulated voltage sense signal samples into the ventilation band to derive a ventilation signal. Such filtering may be accomplished by a bandpass filter or a combination of highpass and lowpass filters as shown in FIGS. 6A and 6B. In one particular embodiment, highpass filter 430 is a single-pole infinite impulse response (IIR) digital filter that receives the 8-bit digital output signal from A/D converter 425, removing frequency components below its highpass cutoff frequency of approximately 0.1 Hz. Many other different embodiments of highpass filter 430 would also be suitable. Highpass filter 430 advantageously further attenuates not only baseline dc components of the transthoracic impedance but also any dc offset voltages created by A/D converter 425. The output of highpass filter 430 is provided to adaptive lowpass filter 435. Lowpass filter 435 receives the output signal of highpass filter 430 and attenuates frequency components of the signal that exceed the lowpass cutoff frequency of adaptive lowpass filter 435. The signal components attenuated by the lowpass filter 435 include the cardiac stroke signal, resulting from changes in blood volume in heart 115 as it contracts during each cardiac cycle.

3. Noise Reduction by Adjustment of Excitation Current

The voltage signals generated at the voltage sensing electrodes can be corrupted by noise produced by external sources in the environment. Such external sources produce current fields in the thoracic cavity that are sensed by the sense electrodes and thus add to the impedance signal. If the noise is not removed, the minute ventilation that is derived from the impedance signal will not accurately reflect the subject's true exertion level and the pacing rate will not be adjusted correctly The voltage sense signal can be thought of as made up of two superposed components: an impedance signal component due to the voltage drop between the sense electrodes caused by the excitation current field in the thoracic volume conductor, and an external field component due to the impression of additional electric fields from noise sources external to the exciter such as the heart or electronic devices outside the body. It is only the impedance signal component that is of interest in measuring minute ventilation, and the external field component is unwanted noise distortion. As described above, a minute ventilation sensor may utilize a bipolar excitation current waveform in order to derive a transthoracic impedance signal from which minute ventilation can be measured. An advantage of using a bipolar waveform in this manner is that most of the external field noise in the voltage sense signal can be removed without distorting the impedance signal.

A highpass FIR filter for removing external field noise can be implemented by sampling the voltage sense signal while excitation current is injected and computing a moving average of an even number of samples with filter coefficients that alternate in sign. Such a filter would have its maximum pass frequency at a frequency equal to half the sampling rate. This is sometimes called the Nyquist frequency and is the highest frequency that can be unambiguously represented in a discrete time signal. The filter would therefore effectively remove frequency components of the voltage sense signal that are appreciably lower than the Nyquist frequency. This would be desirable in the case of the external field component of the voltage sense signal, but it would also remove the impedance signal. By sampling the voltage sense signal during successive phases of a bipolar excitation current waveform, however, so that the polarity of the excitation current varies with the sign of the filter coefficient used to compute the moving average, the moving average of the impedance signal component becomes a lowpass filter instead of a highpass filter. The cutoff frequency of this lowpass filter would normally be much higher than the highest frequency of the impedance signal. The external field component of the voltage sense signal, on the other hand, does not depend upon the excitation current so that its highpass filtering is unaffected by the polarity of the current waveform.

The result of sampling and filtering a bipolar excitation current waveform is thus the effective removal from the voltage sense signal of external field noise below the Nyquist frequency without distortion of the impedance signal. In an embodiment described above, for example, the voltage sense signal was sampled during each phase of a 25 kHz bipolar excitation current waveform at a sampling rate of 50 kHz and moving averaged over four samples. The Nyquist frequency in that case is thus equal to the excitation frequency of 25 kHz and is well above the upper ventilation frequency of about 1 Hz so that any external field noise within the ventilation band is removed from the voltage sense signal samples. If the voltage sense signal were to be continuously sampled and filtered in this manner, the resulting samples could then be simply filtered into the ventilation band to derive the ventilation signal. Continuous injection of excitation current at such a high frequency, however, is energy intensive and drains the battery of an implantable device too rapidly. In the embodiment described above, therefore, the excitation current waveform is strobed at a strobing frequency of 20 Hz, where each strobe is made up of two cycles that are sampled during each phase to give four samples. The demodulator then computes a weighed average of the samples of each strobe using highpass filter coefficients as described above to remove external field noise, and the successive weighted averages constitute the demodulated samples that are processed further to derive the ventilation signal.

Processing the voltage sense signal by strobing the excitation current waveform, however, is equivalent to a downsampling of the continuously moving averaged samples described above at a sampling rate equal to the strobing frequency. As long as the strobing frequency is more than twice the highest frequency found in the impedance signal, no aliasing distortion of that signal will result. Any frequency components of the external field noise that are above the Nyquist frequency for the strobe sampling operation (i.e., half the strobing frequency) and not removed by the high-pass filtering of the demodulator, however, will be aliased to lower frequencies, including possibly the ventilation band where they will produce distortion of the derived ventilation signal. This effect is most pronounced with external field noise at frequencies close to the excitation frequency or any harmonic thereof since those frequencies are not filtered out by the highpass filtering of the demodulator. In the embodiment described, for example, external field noise close to 25 kHz (or close to any integer multiple of 25 kHz) will be passed through by the demodulator's highpass filter and then aliased by the 20 Hz strobe sampling operation to frequencies below 10 Hz. If the external field noise has any appreciable bandwidth, it will invariably be aliased into the ventilation band where it cannot be removed by the filtering used to derive the ventilation signal.

The present invention relates to a method and system for reducing the effects of external field noise by adjustment of the excitation current. Adjustment of the excitation current may involve adjusting the excitation frequency in order to modify the frequency response of the demodulator highpass filter and/or adjusting the excitation current amplitude in order to change to signal-to-noise ratio. The adjustment of the excitation current is performed in accordance with a noise level detected by a noise detection operation. Such a noise detection operation may be initiated by the controller, either periodically or upon receiving a command from an external programmer. As explained below, the noise detection operation involves processing a voltage sense signal when no excitation current is applied so that only external field noise is picked up by the voltage sense electrodes to generate a received noise signal. The received noise signal reflects the noise arising from external sources (e.g., heart signals or any environmental noise sources) as well as internal noise produced by the circuitry of the device. A noise level can then be detected by, for example, determining the average power or amplitude of the noise signal.

In the embodiment shown in FIGS. 6A and 7, the analog demodulator 415 performs a noise detection operation by sampling the output of preamplifier 410 when no excitation current pulses are output. In normal operation, demodulator 415 samples the output of amplifier 410 in response to current pulses 301–304 provided by exciter 150. During a noise detection operation, however, exciter 150 is turned off and current pulses 301–304 are not provided. Switch-closure inputs $\varnothing_1$ through $\varnothing_4$, instead of being synchronized with the excitation pulses, are then independently generated to sample the output of preamplifier 410 at a specified noise sampling rate. In the digital embodiment of FIG. 6B, the analog-to-digital converter 425 is made to sample the preamplifier output at the specified noise sampling rate. If the noise sampling rate is made equal to the sampling rate used during normal operation, the received noise signal will reflect the same noise that would be added to the impedance signal. The frequency response of the highpass filter implemented by the weighted averaging varies with the sampling rate so that the filter maximally passes frequencies near one-half the sampling rate (i.e., the Nyquist rate) or any harmonic thereof. In the embodiments described above, where the each phase of the excitation current waveform is sampled, this is equal to the excitation frequency. By varying the sampling rate during a noise detection operation, a noise sampling rate can be found where the detected noise level is at a minimum. The excitation frequency can then be adjusted accordingly so the sampling rate during normal operation is equal to the noise sampling rate that passes a minimum amount of noise.

In another embodiment, the received noise signal from the demodulator may be further processed in the same manner as a voltage sense signal during normal operation so that the noise signal is filtered into the ventilation band. The noise level is than detected from this filtered signal in order to reflect the actual noise that adds to the ventilation signal. This may be useful where the external field noise has an extremely narrow bandwidth and can be aliased outside of the ventilation band by proper adjustment of the strobing frequency.

The amplitude of the excitation current may also be adjusted by the controller in accordance with a detected noise level. For example, if the noise level detected as described above is so high that an inadequate signal-to-noise ratio would result with the excitation current amplitude presently being used, the excitation current amplitude can be increased to increase the signal-to-noise ratio. Conversely, if the detected noise level is low, it may be possible to decrease the excitation current amplitude and still maintain an adequate signal-to-noise ratio, thus saving battery power. Adjustment of the excitation current amplitude in this manner may also be employed in conjunction with the adjustment of the excitation frequency as described above. In that case, the excitation current amplitude is either increased or decreased in accordance with the noise level detected at a particular noise sampling rate found to pass a minimum amount of noise.

In another embodiment, the gain of demodulator 415 is different during a noise detection operation. This is accomplished in the analog demodulator by sampling the voltage sense signal onto switched-in noise sampling/integration capacitor 630 during noise detection instead of integration capacitor 660. For example, the noise sampling/integration capacitor 630 used during noise detection may be different in value from a corresponding integration capacitor 660 used during normal operation of demodulator 415 to provide an increased gain and more sensitive noise detection.

Figure 8:
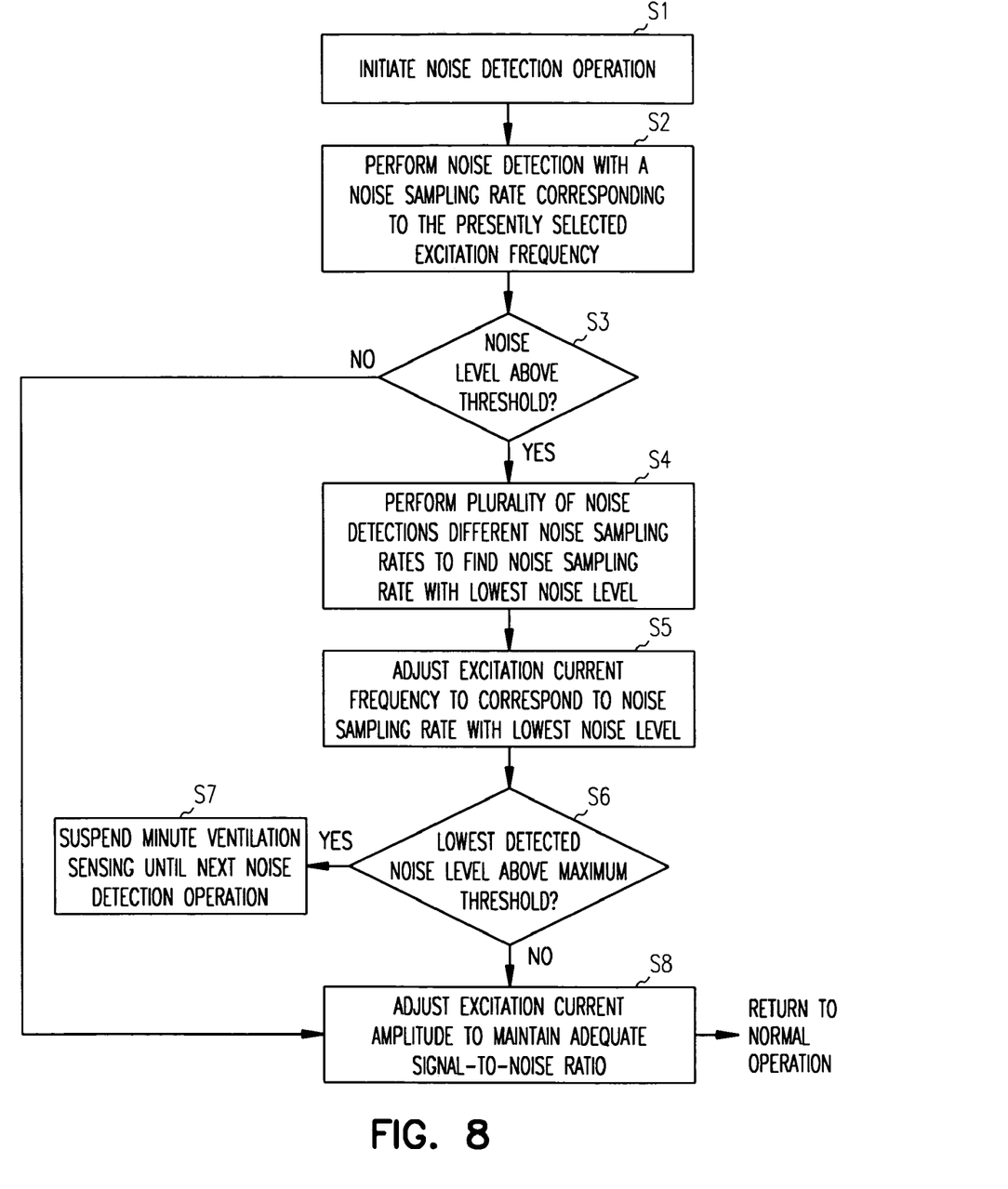
FIG. 8 is a flowchart of an exemplary algorithm for adjusting the excitation current in accordance with a detected noise level.

An exemplary algorithm for adjusting the excitation current in accordance with a detected noise level as may be performed by the controller 165 is illustrated in FIG. 8 as steps labeled S1 through S6. At periodic intervals or upon a command from an external programmer, the controller initiates a noise detection operation at step S1. The noise detection operation is initially performed with a noise sampling rate equal to the sampling rate used in normal operation with the presently selected excitation frequency at step S2. If the detected noise level is below a programmed threshold value as tested at step S3, the device returns to normal operation after possibly adjusting the excitation current amplitude downward to still maintain an adequate signal-to-noise ratio at step S8. In the case of an analog demodulator, a noise comparator 635 as shown in FIG. 7 may be used to determine whether the detected noise is above or below the threshold value. If the detected noise level is above the threshold value, the device at step S4 performs a plurality of noise detection operations while cycling through a number of different noise sampling rates that correspond to available excitation frequencies in order to find the noise sampling rate that results in the lowest detected noise level. The device may then adjust the excitation frequency to correspond to that noise sampling rate at step S5. The device also compares the lowest detected noise level so detected with the programmed threshold value in order to adjust the excitation current amplitude to maintain an adequate signal-to-noise ratio at step S8. At prior step S6, the lowest detected noise level is tested to see if it is above a programmed maximum threshold value such that an inadequate signal-to-noise ratio results even when the excitation current is amplitude is maximally increased. If so, the device may be further programmed to enter a reversion mode in which minute ventilation sensing is temporarily disabled as shown by step S7. The device then continues operating in the reversion mode until the next noise detection operation is performed.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A minute ventilation sensing device, comprising:
   excitation current electrodes for imposing a current field in the thoracic cavity;
   an exciter for supplying excitation current between the excitation current electrodes as a bipolar excitation current waveform at a specified excitation frequency and amplitude, wherein the excitation current waveform is output as a strobe made up of a specified number of excitation current waveform cycles with each strobe repeated at a specified strobing frequency;
   voltage sense electrodes for generating a voltage sense signal corresponding to a potential difference between two points in the thoracic cavity;
   sampling circuitry for sampling the voltage sense signal during the excitation waveform strobe at a specified sampling rate that corresponds to the excitation frequency;
   circuitry for initiating a noise detection operation wherein the voltage sense signal is sampled when no excitation current is supplied and the samples are then processed to detect a noise level; and,
   circuitry means for adjusting the excitation current in accordance with the detected noise level, wherein the excitation current adjusting circuitry means adjusts the excitation current amplitude in response to a detected noise level in order to approximately maintain a specified signal-to-noise ratio.

2. The device of claim 1 wherein the sampling rate corresponding to an excitation frequency is equal to twice the excitation frequency.

3. The device of claim 1 further comprising circuitry for causing a noise detection operation and excitation current adjustment to be performed periodically.

4. The device of claim 1 further comprising:
   a demodulator for generating a weighted average of the voltage sense signal samples of each strobe with a filter coefficient for each sample that is positive or negative in accordance with the polarity of the excitation current waveform such that an impedance portion of the voltage sense signal is low-pass filtered while an external field portion of the voltage sense signal is high-pass filtered;
   circuitry for filtering the demodulated voltage sense signal samples into a ventilation band to thereby generate a ventilation signal; and,
   circuitry for deriving a signal proportional to minute ventilation from the ventilation signal.

5. The device of claim 4 wherein the voltage sense signal samples are filtered by a demodulator with weighting coefficients that high-pass filter the samples in order to detect a noise level during a noise detection operation.

6. The device of claim 5 wherein the weighting coefficients for filtering the voltage sense signal samples during a noise detection operation are equal to the weighting coefficients for filtering the voltage sense signal samples of an excitation current waveform strobe.

7. The device of claim 5 wherein the voltage sense signal signals are further filtered into the ventilation band in order to detect a noise level during a noise detection operation.

8. The device of claim 4 further comprising circuitry for varying the sampling rate during a noise detection operation over sampling rates corresponding to possible excitation frequencies that the exciter may generate in order to determine an excitation frequency that passes a minimum amount of noise into the ventilation band.

9. The device of claim 8 wherein the excitation current adjusting circuitry adjusts the excitation frequency to a value corresponding to a sampling rate that passes a minimum amount of noise into the ventilation band during a noise detection operation.

10. The device of claim 4 wherein the sampling circuitry is incorporated into the demodulator which generates a weighted average of the voltage sense signal samples of each strobe in the analog domain.

11. The device of claim 4 further comprising an analog-to-digital converter for digitizing the sampled voltage sense signals and wherein the demodulator is implemented as a digital filter.

12. The device of claim 4 further comprising an analog-to-digital converter for digitizing the demodulated voltage sense signal samples.

13. A cardiac rhythm management device, comprising:
   a sensing channel for detecting intrinsic cardiac activity;
   a pacing channel for pacing the heart;

a controller for delivering paces in accordance with a programmed mode as modulated by a minute ventilation sensor;

a minute ventilation sensor, comprising:

excitation current electrodes for imposing a current field in the thoracic cavity;

an exciter for supplying excitation current between the excitation current electrodes as a bipolar excitation current waveform at a specified excitation frequency and amplitude, wherein the excitation current waveform is output as a strobe made up of a specified number of excitation current waveform cycles with each strobe repeated at a specified strobing frequency;

voltage sense electrodes for generating a voltage sense signal corresponding to a potential difference between two points in the thoracic cavity;

sampling circuitry for sampling the voltage sense signal during the excitation waveform strobe at a specified sampling rate that corresponds to the excitation frequency;

a demodulator for generating a weighted average of the voltage sense signal samples of each strobe with a filter coefficient for each sample that is positive or negative in accordance with the polarity of the excitation current waveform such that an impedance portion of the voltage sense signal is low-pass filtered while an external field portion of the voltage sense signal is high-pass filtered;

circuitry for filtering the demodulated voltage sense signal samples into a ventilation band defined by an upper ventilation frequency and a lower ventilation frequency to thereby generate a ventilation signal;

circuitry for deriving a signal proportional to minute ventilation from the ventilation signal;

circuitry for initiating a noise detection operation wherein the voltage sense signal is sampled when no excitation current is supplied and the resulting samples are processed to detect a noise level; and, circuitry means for adjusting the excitation current in accordance with the detected noise level, wherein the excitation current adjusting circuitry means adjusts the excitation current amplitude in response to a detected noise level in order to approximately maintain a specified signal-to-noise ratio.

14. A method for sensing minute ventilation, comprising:

imposing a current field in the thoracic cavity as a bipolar excitation current waveform at a specified excitation frequency and amplitude, wherein the excitation current waveform is output as a strobe made up of a specified number of excitation current waveform cycles with each strobe repeated at a specified strobing frequency;

generating a voltage sense signal corresponding to a potential difference between two points in the thoracic cavity;

sampling the voltage sense signal during the excitation waveform strobe at a sampling rate that corresponds to the excitation frequency;

initiating a noise detection operation wherein the voltage sense signal is sampled when no excitation current is supplied and the samples are then processed to detect a noise level; and, adjusting the excitation current in accordance with the detected noise level by adjusting the excitation current amplitude in response to a detected noise level in order to approximately maintain a specified signal-to-noise ratio.

15. The method of claim 14, further comprising:

demodulating the voltage sense signal samples by generating a weighted average of the voltage sense signal samples of each strobe with a filter coefficient for each sample that is positive or negative in accordance with the polarity of the excitation current waveform such that an impedance portion of the voltage sense signal is low-pass filtered while an external field portion of the voltage sense signal is high-pass filtered;

filtering the demodulated voltage sense signal samples into a ventilation band to thereby generate a ventilation signal; and, deriving a signal proportional to minute ventilation from the ventilation signal.

16. The method of claim 15 wherein the sampling rate corresponding to an excitation frequency is equal to twice the excitation frequency.

17. The method of claim 15 further comprising adjusting the excitation current amplitude in accordance with the detected noise level in order to approximately maintain a specified signal-to-noise ratio.

18. The method of claim 15 further comprising varying the sampling rate during a noise detection operation over sampling rates corresponding to different excitation frequencies in order to determine an excitation frequency that passes a minimum amount of noise into the ventilation band.

19. The method of claim 18 further comprising adjusting the excitation frequency to a value corresponding to a sampling rate that passes a minimum amount of noise into the ventilation band during a noise detection operation.

20. The method of claim 15 wherein the voltage sense signal samples are filtered with weighting coefficients that high-pass filter the samples in order to detect a noise level during a noise detection operation.

21. The method of claim 20 wherein the weighting coefficients for filtering the voltage sense signal samples during a noise detection operation are equal to the weighting coefficients for filtering the voltage sense signal samples of an excitation current waveform strobe.

22. The method of claim 20 further comprising filtering the voltage sense signal signals into the ventilation band in order to detect a noise level during a noise detection operation.

* * * * *

UNITED STATES PATENT AND TRADEMARK OFFICE
CERTIFICATE OF CORRECTION

PATENT NO.        : 7,092,757 B2                                            Page 1 of 1
APPLICATION NO.   : 10/195135
DATED             : August 15, 2006
INVENTOR(S)       : Larson et al.

It is certified that error appears in the above-identified patent and that said Letters Patent is hereby corrected as shown below:

On the Title page, in item (56), under "Other Publications", in column 2, line 3, after "2002," insert -- Attorney Docket No. 279.443US1, --.

On the Title page, in item (57), under "Abstract", in column 2, line 2, after "with" delete "a" and insert -- an -- therefor.

In the Drawing
On Sheet 7 of 8, in FIG. 7 (below Numeral 635), delete "$Q_{AZ}$" and insert -- $\varnothing_{AZ}$ --, therefor.

Signed and Sealed this

Twelfth Day of December, 2006

JON W. DUDAS
*Director of the United States Patent and Trademark Office*